(12) United States Patent
Kley et al.

(10) Patent No.: US 6,172,743 B1
(45) Date of Patent: Jan. 9, 2001

(54) TECHNIQUE FOR MEASURING A BLOOD ANALYTE BY NON-INVASIVE SPECTROMETRY IN LIVING TISSUE

(75) Inventors: Vic Kley, Berkeley, CA (US); Melvin Schwartz, Bellport, NY (US)

(73) Assignee: Chemtrix, Inc., Mill Valley, CA (US)

( * ) Notice: Under 35 U.S.C. 154(b), the term of this patent shall be extended for 0 days.

(21) Appl. No.: 08/852,168

(22) Filed: May 6, 1997

Related U.S. Application Data

(63) Continuation of application No. 08/436,682, filed on May 8, 1995, now abandoned, which is a continuation of application No. 08/437,113, filed on May 5, 1995, now abandoned, which is a continuation of application No. 08/182,312, filed on Jan. 14, 1994, now abandoned, which is a continuation of application No. 07/958,025, filed on Oct. 7, 1992, now abandoned.

(51) Int. Cl.[7] ................................................. G01N 33/48
(52) U.S. Cl. ............................................ 356/39; 128/633
(58) Field of Search ............................ 128/633; 356/39, 356/40, 41, 323, 324, 325

(56) References Cited

U.S. PATENT DOCUMENTS

| | | | |
|---|---|---|---|
| 4,266,554 | 5/1981 | Hamaguri | 128/633 |
| 4,561,731 | 12/1985 | Kley | 350/510 |
| 4,653,498 | 3/1987 | New, Jr. et al. | 128/633 |
| 4,730,621 | 3/1988 | Stott | 128/667 |
| 4,738,266 | 4/1988 | Thatcher | 128/664 |
| 4,883,055 | 11/1989 | Merrick | 128/633 |
| 4,892,101 | 1/1990 | Cheung et al. | 128/633 |
| 4,927,264 | 5/1990 | Shiga et al. | 356/41 |
| 4,975,581 | 12/1990 | Robinson et al. | 250/339 |
| 5,028,787 | 7/1991 | Rosenthal et al. | 250/341 |
| 5,070,874 | 12/1991 | Barnes et al. | 128/633 |
| 5,137,023 | 8/1992 | Mendelson et al. | 128/633 |
| 5,313,941 | 5/1994 | Braig et al. | 128/633 |
| 5,337,745 | 8/1994 | Benaron | 128/633 |
| 5,348,003 | * 9/1994 | Caro | 356/39 |

OTHER PUBLICATIONS

Heise et al., "Multivariate determination of glucose in whole blood by attenuated total reflection infrared spectroscopy," *Anal. Chem.*, vol. 61:2009 (1989).

Peuchant et al., "Determination of serum cholesterol by near–infrared reflectance spectrometry," *Anal. Chem.*, vol. 59:1816–1819 (1987).

Rabinovitch et al., "Noninvasive glucose monitoring of the aqueous humor of the eye," *Diabetes Care*, vol. 5 (No. 3); pp. 254–258 (May–Jun. 1982).

* cited by examiner

Primary Examiner—Frank G. Font
Assistant Examiner—Roy M. Punnoose
(74) Attorney, Agent, or Firm—Townsend and Townsend and Crew LLP

(57) ABSTRACT

A device for non-invasively measuring an analyte within the body uses a source of light to illuminate a tissue component, then detects and measures the light during more than one selected time period. The light source may be tuned or coupled with one or more filters to provide a selected light spectrum. The tissue component may be any extremity which contains blood and can conduct light, preferably a finger or ear lobe. The detector selects a wavelength or group of wavelengths. The light source may be varied, the source filters may be modulated, or the detector may be sampled at selected times. In general, it is desirable to take one measurement during maximum blood flow in the tissue component and a second measurement during minimum blood flow. The blood flow may be modified by pressure or temperature. The minimum blood flow measurement provides a reference to be subtracted from the signal for the analyte of interest in blood.

14 Claims, 5 Drawing Sheets

TECHNIQUE FOR MEASURING A BLOOD ANALYTE BY NON-INVASIVE SPECTROMETRY IN LIVING TISSUE

CROSS REFERENCE TO RELATED APPLICATIONS

This application is a continuation of application Ser. No. 08/436,682, filed May 8, 1995, which was a continuation of Ser. No. 08/437,113, filed May 5, 1995, which was a continuation of Ser. No. 08/182,312, filed Jan. 14, 1994, which was a continuation of application Ser. No. 07/958,025, filed Oct. 7, 1992, all now abandoned.

FIELD OF THE INVENTION

The present invention relates to measuring the concentration of blood analytes such as glucose, cholesterol, potassium, bilirubin and other substances of interest present in the blood and tissue. Particularly, the invention relates to measurements made with an electromagnetic source of radiation in the wavelength range of 0.4 to 150 microns interacting with blood containing tissue so as to differentiate specific blood analytes from any contained or trapped in the tissue which is not freely transported through the blood.

BACKGROUND

It is frequently necessary to determine the concentration of various blood analytes when maintaining or treating mammals, including humans. An important example is the diabetic, whose glucose must constantly be monitored. Presently, diabetic blood is sampled invasively, typically through a finger prick or by drawing a blood sample. Other analytes of potential interest include lipids, cholesterol, serum proteins and electrolytes.

Much work has been done to monitor glucose by various non-invasive methods. These methods include infrared spectrophotometry. See Barnes et al., U.S. Pat. No. 5,070,874 (assigned to Biocontrol Technology, Inc.), Rosenthal et al., U.S. Pat. No. 5,028,787 (assigned to Futrex, Inc.), Dähne et al., European Patent Publication No. 0,160,768 (Batelle Memorial Institute), and Robinson et al., U.S. Pat. No. 4,975,581 (assigned to the University of New Mexico). Other methods include alternative optical means such as that proposed in the article "Noninvasive Glucose Monitoring of the Aqueous Humor of the Eye" by Rabinovitch et al., Diabetes Care, Vol. 5 (No. 3): pp. 254–258 (May–June 1982). Other methods have been devised, including sampling of interstitial fluid in the mouth (unpublished communication from Mary Anne MacGillivray and Richard Battelle of Healthcraft International, Pasadena, Calif., 1988). Although non-invasive measurements can be made, all known prior art methods fail to distinguish whether an analyte, e.g. glucose, is in the subject's bloodstream or in surrounding tissue. This can result in incorrect and inappropriate determinations because of chemical interactions of the same or a spectrophometrically similar analyte located in the tissue where transport and utilization is distinctly different from the analyte moving through veins and arteries.

In addition, all prior methods suffer from low signal to noise of the spectrophotometric signals due to limitations of the light source and the limited resolution of spectral means such as gratings, prisms, filters, Hadamard or Fourier Transform (interferometric) spectrometers. These limitations result in poor analyte resolution or lengthy sample times, unnecessarily confining or restricting the movements of the subject or patient being tested.

In the known, non-invasive measurement prior art, no effort is made to distinguish analyte in the blood from that in tissue or interstitial fluids. Additionally, previous workers such as Robinson, Rosenthal and others limit spectroscopic non-invasive measurements to the near infrared region of the electromagnetic spectrum ignoring the visible and the medium and long infrared regions, limiting performance, accuracy, and range of blood analytes which can be detected and resolved.

Additionally, many medical conditions cause a physiological change in certain tissues which are otherwise suitable for non-invasive monitoring. For example, diabetics frequently suffer substantial reductions in peripheral blood flow to peripheral tissue such as the ear or finger.

Current methods and devices fail to provide adequate information about blood flows, blood volumes, and tissue temperatures at and across the tissue field. This information may be important to the determination of blood analytes and/or the proper medical evaluation of the blood analyte level and/or the medical condition, and temperature dependant behavior of the analyte and tissue. Current methods and devices also fail to provide information about the blood analytes located specifically in the tissue and interstitial fluid.

SUMMARY OF THE INVENTION

The present invention includes a device for non-invasively measuring an analyte within the body of a mammal. The device uses a source of light at one or more selected wavelengths for illuminating a tissue component of a mammal, then detects the light and measures the light during more than one selected time period. The light source may be a flash tube and a halogen lamp, which may have an envelope of quartz, sapphire, silicon, germanium, or other material which can pass selected light wavelengths. The light source may also be a laser, a laser diode, an LED, an array of lasers, laser diodes, or LEDs, any of which may be tuned to emit a selected range of wavelengths. Any of these light sources may be coupled with one or more filters, each of which passes one selected wavelength or selected wavelengths, which may be continuous or discontinuous. The filters may be switched as well, passing light or not light depending on the state of the filter.

The tissue component may be any extremity which contains blood and can conduct light. Preferred extremities are the finger and the ear lobe, but most any extremity will do if it will conduct any light. In one embodiment, light can be reflected from most any tissue, including deep tissue, an arm, a leg, the torso, scalp or the head.

The detector may be a charge coupled device, a photomultiplier, or other device capable of converting incident light into an electrical signal. The detector may be tuned to be sensitive to a selected wavelength or group of wavelengths, or may be coupled with one or more filters sensitive to a selected wavelength or group of wavelengths.

To provide signals at selected times, the light source may be varied, the source filters may be modulated, or the detector may be sampled at selected times, or a combination of the above. In general, it is desirable to take one measurement during maximum blood flow in the tissue component and a second measurement during minimum blood flow. The minimum blood flow measurement provides a reference for the other reading, allowing all background signals from tissue, bone, etc. and any analyte bound in tissue to be subtracted from the signal for the analyte of interest in blood. It may be helpful to take measurements at repeated blood flow cycles in order to improve signal to noise in a signal.

The difference in maximal and minimal blood flow can be accentuated by reducing the blood flow in the tissue region, for example by compression of the tissue. An inflatable cuff around a finger or a clamp on an ear lobe are useful examples. In addition, the temperature of the tissue can be modified through heating or cooling elements. A restrictive cuff around the base of a finger can exclude blood or can entrap blood for additional measurements.

The method of analysis includes measuring the analyte during both high and low blood flow. By selecting a variety of wavelengths and using multivariate analysis, one or more analytes can be distinguished from other blood and tissue components.

It is therefore an object of this invention to provide a new and improved apparatus for the non-invasive measurement of blood analytes using a broad range of electromagnetic wavelengths.

Another object of this invention is to provide a means to distinguish a blood analyte from the same or a similar analyte in the tissue or interstitial fluids.

Yet another object of this invention is to provide an apparatus which measures both blood analytes and tissue/interstitial analytes.

Another object of this invention is to provide an apparatus which measures blood flow and blood volume in vasculature and also to provide an apparatus which measures blood flows and blood volumes across a tissue field.

Another object of this invention is to measure temperature within a tissue field and also to provide an apparatus which measures temperature across the tissue field.

Another object is to provide a new apparatus for non-invasive measure of blood analytes and tissue analytes which is suitable for clinical applications.

Yet another object of this invention is to provide an apparatus which provides an improved light source, improved signal to noise means and spectrophotometric means.

Another object is to provide a new apparatus, suitable for home applications, for non-invasive measure of blood analytes and tissue analyte.

DETAILED DESCRIPTION OF THE INVENTION

Figure 1:
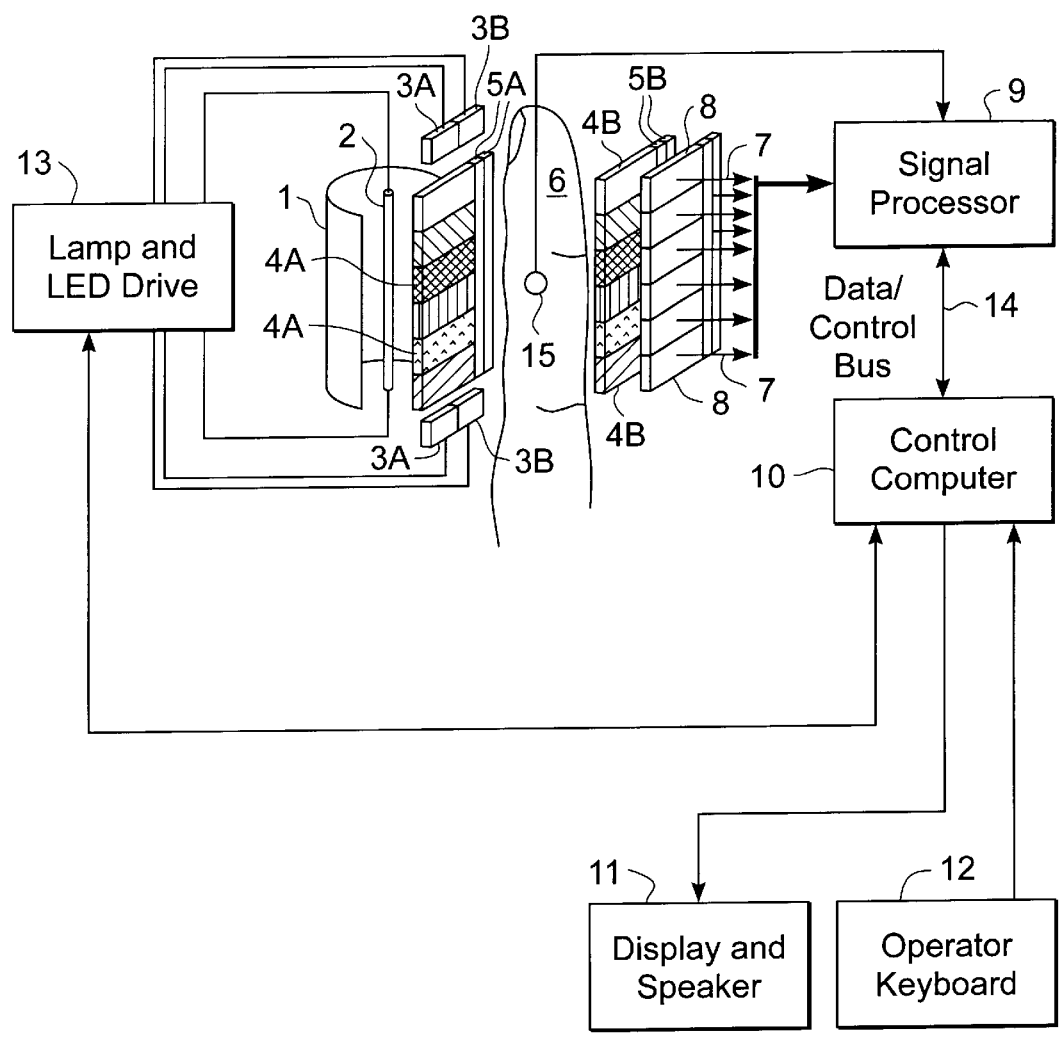
FIG. 1 illustrates one embodiment of the invention structured for the non-invasive monitoring of the finger using a flash lamp, spectral filters over the lamp and detectors.

The basic device of the invention includes a light source, a detector, and analytical hardware and/or software to provide measurement of an analyte to an operator. An operator may be a health care professional or, preferably, a patient being tested, who can operate the device and can read test results without assistance. The basic method of the invention uses the device to measure the analyte at two or more times. In addition, the device and method include various ways of modifying blood flow to improve detection of the analyte.

The analyte may be glucose, lipids, cholesterol, serum proteins or other blood components. Many components which cannot be detected directly can be measured by combining a marker with something which combines with the analyte, for example an antibody for some protein, with the antibody bound to a selected optically active component, which might include a fluorophore or optical "tag" with a characteristic absorption spectrum or other optical characteristics such as a specific interaction with polarized light. Spectra of many target analytes are well known. See, for example, spectra shown in FIGS. 2, 3 and 5 of Barnes et al., U.S. Pat. No. 5,070,874, or wavelengths of interest noted in Rosenthal et al., U.S. Pat. No. 5,028,787.

Using the known spectral characteristics of the analyte to be measured, electromagnetic energy from the light source is passed through the tissue being sampled (typically the ear lobe or finger) and then to the detectors which develop signals which are then converted to digital values and processed by a digital computer. The measured values may be used immediately or stored for subsequent analysis. After a change in the blood volume, the process is repeated and new values are converted, processed and stored. The process may be repeated at high (zenith, systole) and low (nadir, diastole) blood volumes to obtain average values at each blood volume to improve the signal to noise ratio. In addition, one or more reference signals can be detected at each measurement in order to monitor the light source itself and compensate for frequency or intensity variations of the light source.

One or more temperature sensors in the tissue field are used to correct raw values in the calculation of the analyte quantitative measures. In parallel with the temperature measurement, a photoplethysmometer measures blood flow and volume by monitoring arterial hemoglobin using red and near infrared light emitting diodes and detectors across the tissue field, preferably at the base and upper portion of the finger or inner and outer portions of the ear lobe. This measurement can be corrected for oxygenation of the hemoglobin using methods well known in the art.

Several conditions may limit the usefulness of the measurement of analyte. If these conditions are not within allowable limits, the user will be signalled that the reported measurement is not reliable or there may be no measurement reported to the user at all. If the difference between systole and diastole is too small, if the temperature values are substantially inappropriate for proper measure of the tissue, if the differential between the measured tissue regions is too great, or if oxy-hemoglobin levels are outside selected limits, then the instrument may signal the user that no reading can be obtained or reported. In addition, the instrument will notify the operator that an accurate measurement cannot be made.

If the temperature and hemoglobin readings are within limits, depending on measurement conditions, then the timing information about peak and nadir blood flow is used to time the next measurement for the blood analyte of interest.

Light Source

The light source for the device of this invention can take several different forms. One form is one or more flash lamps selected to deliver high output of wavelengths of interest.

Other light sources include a continuous lamp or a laser or LED. Sunlight may be focussed or directed for use as a light source. Other potential light sources are known in the art. In general, the light source should be able to provide a useful flux of radiation over at least part of the wavelength range of 0.4 to 150 microns, or visible light through far infrared. The light source is preferably capable of low power operation so that the device can be made portable and battery powered.

Any of the light sources described below may be designed or adjusted to provide a light spectrum of interest or can be filtered through a dispersive element to provide the desired spectrum. Another useful light source is a monochrometer, preferably one which can be scanned or tuned to several selected wavelengths. In addition, the light can be passed through a polarizing filter, for example to provide circularly polarized light. Filters may be relatively planar or may be bent or otherwise configured to adapt the device to a tissue of interest. One skilled in the art will recognize many potential combinations of illumination sources and filters suitable for use with this invention.

One preferred light source is one or more flash lamps whose gas and envelope are suited to produce electromagnetic radiation of frequency appropriate to the range of frequencies required to measure the analyte. Xenon and an envelope of sapphire and/or silicon are appropriate to measure glucose and other analytes having activity in the near, mid and far infrared regions. Other gases and materials may also be suitable.

The light source may contain wavelengths that are not of interest, so in general the light source will be coupled with one or more dispersive elements to select one or more wavelengths for illuminating the tissue field. One useful dispersive element is an interference filter, the manufacture and use of which is well known in the art. Other useful dispersive elements include a dispersive grating, such as a holographic grating or standard rule grating, or a phase plate. Other dispersive devices are known in the art. If the light source does not include unwanted wavelengths, no dispersive elements are required. For example, the light source may be a monochrometer which produces selectable, desired wavelengths and excludes unwanted wavelengths without need for a dispersive element.

In addition, the light source may be coupled with means to channel or focus light on a selected area of a tissue field. This may be achieved through use of a collimated light source, through focusing using a positive lens, using fiber optics or some combination of these techniques alone or with other means know to those skilled in the art. A lens or reflector may be refractive or reflective, and may use a phase plate or combination of optical elements, preferably with a net positive effect in concentrating light in a selected area. A ray entering a positive optical system at a certain angle of incidence relative to the optical axis exits the optical system at a smaller or inward angle. In general, a reflective system is preferred to a refractive system.

A second useful light source is one or more lasers, laser diodes, or light emitting diodes with outputs selected or designed to correspond to spectral frequencies appropriate to the analyte of interest. The diodes may be individual elements or the diodes may be made on a single substrate and individually tuned during manufacturing to provide the desired frequency characteristics. Furthermore the diode array may include frequencies suitable for multiple analytes, and selected for use by the controlling computer and operator.

Another useful light source is one or more fixed, broad-spectrum light sources such as a tungsten, tungsten-halogen or a flash lamp with appropriate envelope which provides electromagnetic energy to an electrically tunable etalon to provide a series of spectral bands appropriate to the analyte.

Another useful light source includes multiple electronic light switches overlaid by appropriate spectral filters and polarizers combined with the sources above to create a computer-controlled, single set or sequential series of spectral bands appropriate to the analyte of interest.

Any or all of the light sources may be designed to emit circularly polarized light or may be filtered to provide circularly polarized light.

Detection and Analysis

A detector may be a charge-coupled device (CCD), a photomultiplier or other device capable of converting light into electricity. The detector may respond to a broad range of wavelengths or may be responsive to a select group of wavelengths. A detector may be coupled with a dispersive element, similar or identical to the dispersive element coupled to the light source. Focusing components, such as a positive lens or mirror, phase plate or combination, may also be included on the detector side. Each optical element, such as a lens or a dispersive element, is preferably complementary to the corresponding optical element in the light source. For example, matching mirrors may be used or interference filters with similar or identical performance and characteristics may be used in both the light source and the detector. A suitable detector may be made of germanium, indium gallium arsenide, platinum silicide, lead sulfide, indium antinomide, silicon, mercury cadmium telluride, mercury manganese telluride or other materials well known in the art. One preferred detector is an array of silicon diode detectors coupled with a suitable dispersive element, such as a holographic grating such that only a relatively narrow range of wavelengths falls on a single diode detector. Alternatively, a suitable dispersive element can be moved to scan different wavelengths across a single detector or small array of detectors.

A variety of detector configurations are useful but the general feature is that the detector can provide some response to incident wavelengths of interest. The detector is preferably a series of detectors, each of which may be tuned to be responsive to one or more groups of wavelengths, which may be continuous or discontinuous, generally similar or identical to wavelengths in the irradiating light. Each detector may be sensitive to selected wavelengths and may be coupled with a filter to provide a selected response curve. In addition, when an analyte has polarization activity, a right- or left-hand circular polarizing optical element can be used at the source and/or detector to increase the signal to noise ratio. A detector may be selectively sensitive to circularly polarized light, or may be coupled to an appropriate filter.

A combination of sensors can be used to provide a broad spectral response. The area of the dispersive element (e.g. filter) and thus the total radiative flux from a source or collected can be increased or decreased to compensate for the quantum efficiency, spectral response and noise characteristics of a source or detector in each spectral band to be measured.

Light originating from a point source illuminates a local region of the tissue being tested but the tissue typically disperses the illumination across a wider region, typically a significant portion of the tissue. Detecting a corresponding signal at different points provides information about various regions of the tissue and significant portions of the tissue field can be studied. The geometry of illumination and detection illustrated in FIG. 1 shows that light originating from one LED 3 near the base of the finger may be detected through filter SB at one or more selected locations along the filter, including near the base, near the middle or near the top of the finger. Similarly, light originating from a second LED 3 near the top of the finger may be detected through filter 5B at one or more selected locations.

Figure 5:
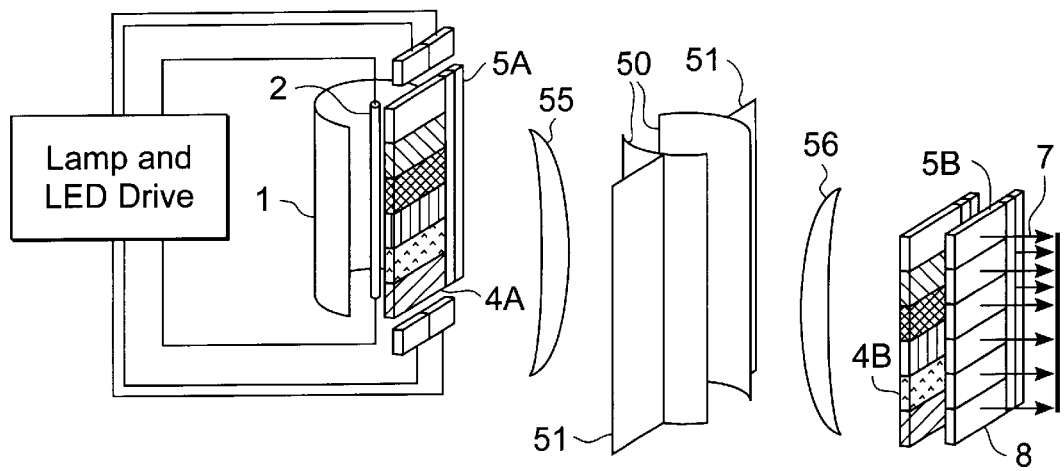
FIG. 5 illustrates a light blocking device to improve signal collection.
Figure 6:
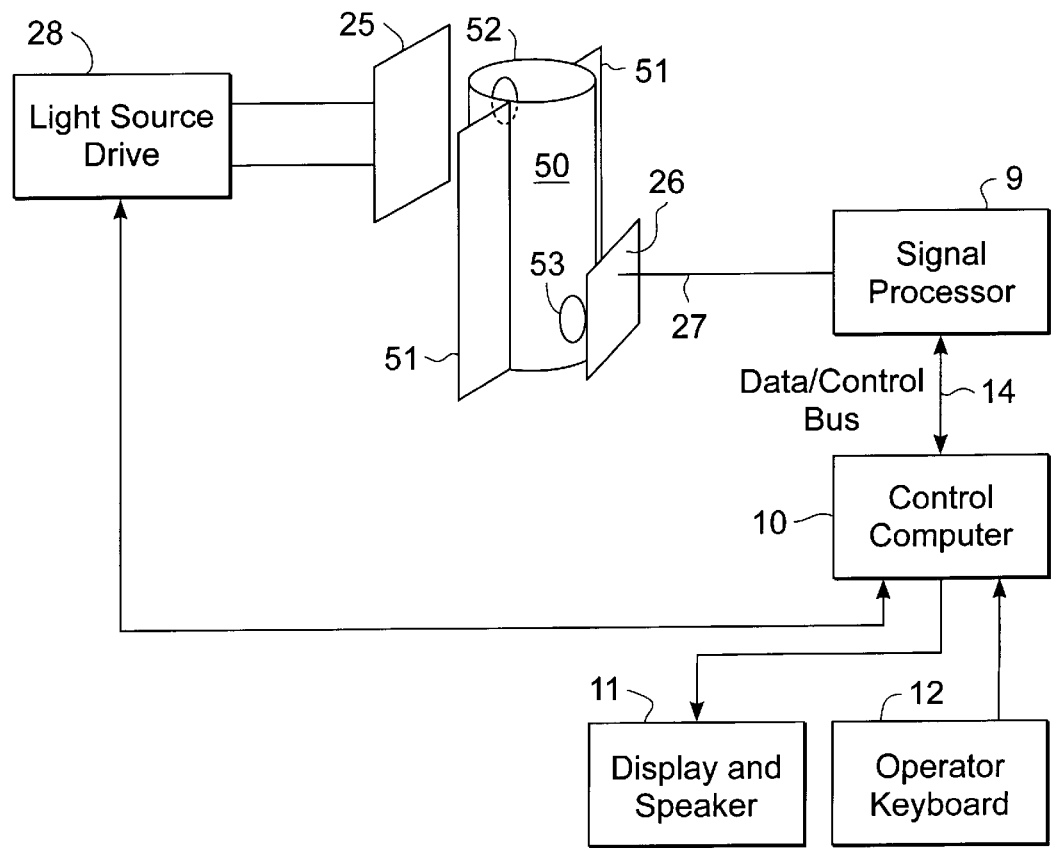
FIG. 6 illustrates the detector offset from the light source to increase the light collection path.

The choice of geometry for illumination or detection can be varied or selected to satisfy engineering criteria such as optimal signal path length, balancing the need for a signal strong enough to be detected against a longer path length, which passes through more of the tissue to be analyzed and therefore with more analyte. In general, the source and detector are aligned on a principal optical axis with any filters generally perpendicular to that axis and the tissue field of interest also generally perpendicular to the optical axis. See FIG. 1. Signal path geometry can be altered by changing the positions of filters 4B relative to corresponding filters 4A to give a longer light path through the tissue. For example, filter 4B corresponding to the lowest filter 4A could be shifted up two positions. See FIG. 5. FIG. 6, discussed below, illustrates offsetting the detector and moving it off the principal optical axis. The plane of the filters in the light source is generally parallel to the plane of the filters in the detector, as shown. A similar configuration may be useful wherein the light source and detector are angled to place each on the principal optical axis and again keep the filters perpendicular to that axis. One skilled in the art will recognize many potential configurations useful with the teachings of this invention.

An array of detectors can be configured to detect light in different areas of the tissue field. One or more detectors may be configured to examine incident light from different sources. Either or both of these configurations may allow some imaging of the tissue field by measuring light passing through selected regions of the tissue field. Alternatively, an array-type light source with different geometrical positions can be coordinated with one or more detectors and can be pulsed selectively to scan the tissue field both in geometry and also in transmission characteristics to provide a spectroscopic scan of the tissue field.

In general, a light source such as a flash tube or a continuous lamp coupled to a switchable filter is preferably pulsed at a known time and a corresponding detector is activated at a corresponding time. A typical method flashes the light source during systole, then again during diastole and cycle may be repeated.

A conventional spectrophotometer pulses the light source in a known manner, typically at a fixed frequency, then the detector is phase-locked to that pulse and frequency. The light sources of the present invention may be pulsed in a selected pattern to facilitate detection. One method illuminates a tissue field over several or many heartbeats. In this case, it is helpful to use the traditional spectrophotometric method of pulsing the light source and phase locking the detector to the source. A light source of switched filters or an array of lasers, laser diodes, or LEDs is particularly well suited to this method.

Referring to FIG. 1, selected signals are detected and directed to a computer, typically a digital computer. An analog signal from detector 8 is converted in signal processor 9 into a digital signal, which is then passed over data/control bus 14 to control computer 10. Control computer 10 can use a variety of analytical techniques to extract information from the detected signal.

In any embodiment of the invention, computing means may be used to combine the results of differentiating the blood analytes from tissue analytes with common algorithmic techniques well known in the art to obtain precise quantitative measures of blood analytes and tissue analytes or other spectrophotometric analytical methods. Such methods include those known as Partial Least Squares, Multivariate Analysis, and Logarithm of the Inverse Reflectance or Transmittance similar to those used or proposed by Heise et al., Anal. Chem. Vol. 61:2009 (1989); DuU et al., J. Food Sci. Vol. 49:1601–1603 (1984); Peuchant et al., "Determination of Serum Cholesterol by Near-Infrared Reflectance Spectrometry," Anal. Chem., Vol. 59:1816–1819 (1987). For consistent measurement and analysis, it is preferable that light for each wavelength or set of wavelengths pass through the identical tissue portion or pass through an equivalent volume of tissue. This might be achieved through a series of parallel light sources and detectors passing through equivalent tissue portions or perhaps by using a variable light source or detector so that all measurements are made through the identical tissue portion.

Water is present in blood and all tissues to some degree. Water absorbs quite strongly at some infrared wavelengths and can interfere with some detection schemes. The absorption spectrum of water is well known and the distribution of water in normal tissue is also well known. In a preferred embodiment, the analytical circuitry compensates for the presence of water by creating a set of scale values for each region of spectral measurement of the blood analyte. The values are adjusted for the magnitude of the difference of peak and minimum blood flow for each region. This set of scale values may be a precalculated table, algorithm or combination of the two. Compensation may be through modification of the light source, e.g. boosting selected wavelengths, or detection, e.g. modifying detection schemes as needed for certain wavelengths. For example, a strongly absorbing water peak may overlap a wavelength region of interest. The effect of the water absorption may be reduced by applying a DC offset to the signal, by processing the signal through a differential op amp, or other methods known by those skilled in the art.

A preferred method of the invention compensates for cellular scattering and fixed common cellular analytes by creating a set of scale values based on the regions of spectral measurement of the blood analyte and the minimum value of the spectral signal obtained at the minimum blood volume. The scale factor is created from the known characteristics of the tissue field e.g. the scale characteristics would be different for the finger which contains muscle, cartilage and bone as opposed to the ear lobe which has no muscle, cartilage or bone. This set of values may be a precalculated table, algorithm or combination of the two.

FIG. 1 illustrates one preferred embodiment of the invention, with a flash lamp, spectral filters over the lamp and detectors to form a complete measurement system. Referring to FIG. 1, lamp and LED drive 13 triggers flash lamp 2. Radiation from flash lamp 2 is reflected and collimated by curved reflector 1 and filtered by source filters 4A and 5A. Spectral filters 4 are one or more filters each designed to pass one or more selected wavelengths of light, typically selected for measuring a selected analyte or group of analytes. Each of filters 4 is typically a bandpass filter for a single wavelength or continuous band of wavelengths. Filter 5 is one or more filters, typically narrow band pass, to pass visible red and infrared light. In general, filters 5 are tuned to analyze hemoglobin at two selected wavelengths and filters 4 are tuned to measure one or more analytes of interest. Light passes through finger 6 and detector filters 4B and 5B, typically identical to the corresponding source filters, and is measured in one or more detectors 8. Detectors 8 are connected through lines 7 to signal processor 9, which in turn is connected through bi-directional data/control bus 14 to control computer 10. Control computer 10 is connected to lamp and LED drive 13 and also to an output device, here display and speaker 11, and an input device, here operator keyboard 12. The temperature of finger 6 is measured by sensor 15, which is connected to signal processor 9.

Control computer 10 initiates a measurement cycle by instructing lamp and LED drive 13 to activate red LEDs 3A and near infrared LEDs 3B, sending red and near infrared radiation through finger 6. The spectrum of LEDs 3 is preferably optimized to measure hemoglobin in finger 6. The signal from LEDs 3 is detected by detectors 8 after passing through filters 5B and the detected signal is passed through signal processor 9 to control computer 10 to evaluate the pulse cycle in finger 6. Using methods known in the art, particularly in the art of plethysmography, selected illuminating frequencies from LEDs 3 provide information on when a pulse begins, peaks and ends. The temperature of finger 6 may be important for certain measurements so the temperature is tested to be sure it comes within acceptable limits. If the pulse information or temperature information indicate that an accurate measurement cannot be made, an appropriate message is sent to display and speaker module 11. If a measurement can be made, the pulse and temperature information can be used by control computer 10 to select when to trigger flash lamp 2, preferably synchronized with a selected blood flow state, e.g. maximum blood flow. Spectral transmission through filters 4 and finger 6 provide information about analytes present in finger 6. The spectral transmission is analyzed in control computer 10 or may be stored for subsequent reduction by analytical routines into blood analyte measurements. Control computer 10 initiates another measurement at the opposite blood flow state from the first measure. For improved signal to noise, multiple sets of signals for each blood flow state may be obtained and averaged. Software routines which remove the effect of water may be employed to improve signal to noise.

Figure 2:
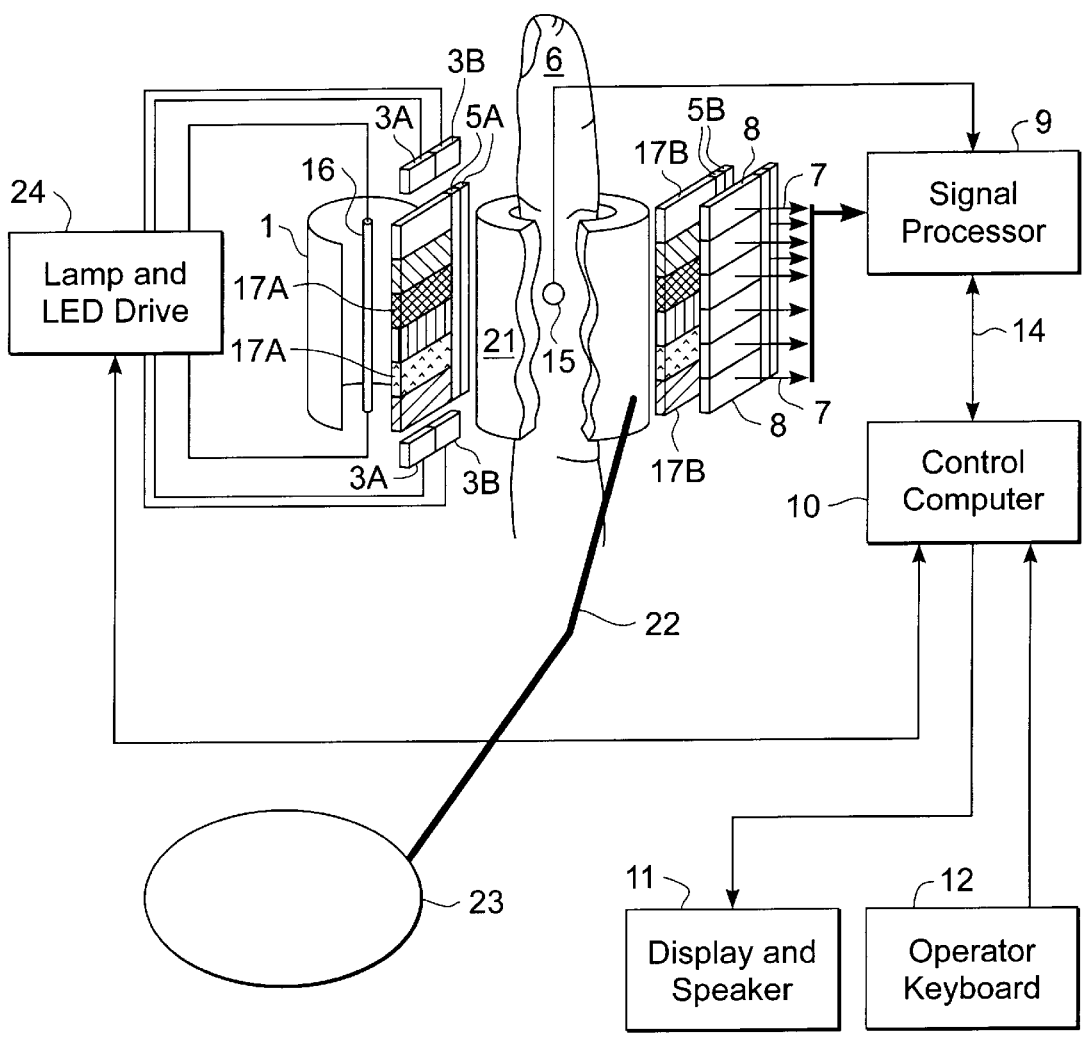
FIG. 2 illustrates a second embodiment of the invention including finger in which an transparent, inflatable cuff with a tungsten halogen lamp, filters and detectors.

FIG. 2 illustrates a second embodiment of the invention, adding an inflatable cuff transparent to the spectral frequencies, combined with a tungsten halogen lamp, filters and detectors to form a complete measurement system. Referring to FIG. 2, this device differs from that of FIG. 1 in using a continuous light source, tungsten halogen lamp 16, in place of flash lamp 2. Lamp and LED drive 24 is optimized for driving a continuous light source. One or more feedback light detectors (not shown) sensitive to one or more frequencies can be added at one or more points near lamp 16 or after filters 17 to provide direct feedback to lamp and LED drive 24 and allow improved control of the light output of lamp 16. The tube of lamp 16 may be of quartz, conventional glass, silicon, sapphire, germanium, or other material suitable for passing necessary light wavelengths.

This device also differs from the first in using one or more spectral signature filters 17. Each of filters 17 may pass a selected group of wavelengths, typically multiple wavelengths, appropriate for measurement of a selected analyte. By contrast, each of filters 4 is typically a bandpass filter for a single wavelength or continuous band of wavelengths. Any of filters 17 may be switchable between relatively transparent and relatively opaque states, allowing modulation of the radiation incident on the tissue being tested. Any of filters 17 may include a circular polarizer in its construction, or may be coupled with a circular polarizer.

Figure 3:
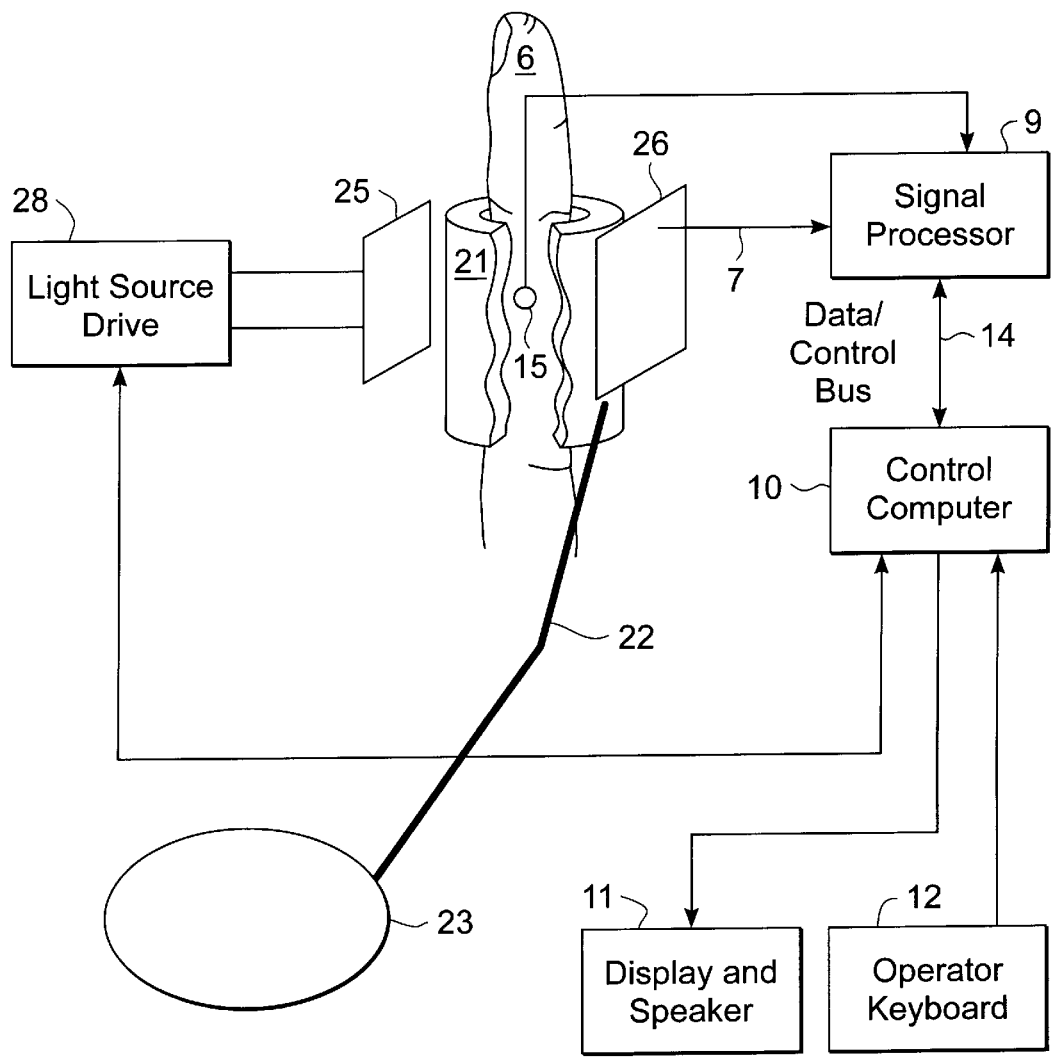
FIG. 3 illustrates a third embodiment of the invention using lasers and light emitting diodes and an inflatable cuff.

FIG. 3 illustrates a third embodiment of the invention using lasers, laser diodes, or light emitting diodes to provide the light source at selected spectral frequencies for analytes to be monitored, combined with a transparent, inflatable cuff. The light source of this device differs from the devices of FIGS. 1 and 2 by using array 25 of LEDs or lasers, driven by light source drive 28. Each element of array 25 can be tuned to provide a selected light wavelength or range of wavelengths. This can be achieved, for example, by selective doping a silicon substrate. This and other methods of tuning LEDs and semiconductor lasers are well known in the art. At least one element of the array can provide the light needed to detect hemoglobin to monitor the pulse, as described above. Detector 26 may also be an array, each element of which is selectively tuned or sensitized for a select light wavelength or group of wavelengths. Each element, or selected elements, in the array can be selectively pulsed to provide a sequential series of distinct radiation pulses (preferably approximately 1 millisecond per pulse) to create a spectral series of visible and near infrared pulses appropriate for a selected analyte. Alternatively, an array of detectors can be placed behind an array of filters 4, filters 17, or other selected filters.

Blood volume modification

This invention uses the subject's own tissue to provide a background reading for analytes present in tissue by measuring the analyte during maximal blood perfusion, e.g. at systole, and again at minimal blood perfusion, e.g. at diastole. Increased blood flow differentials substantially increase the signal to noise ratio for measuring the blood analytes since there is more analyte available during maximum flow conditions. The difference in perfusion can be accentuated by reducing diastolic blood flow or by increasing systolic blood flow. Blood flow can be reduced by compressing the tissue, thereby physically squeezing extra blood out of the tissue, or by temporarily restricting blood flow entering the tissue, e.g. by cooling the tissue, by stimulating the arterioles to decrease incoming blood supply, or by physically restricting blood flow into the tissue. Blood flow can be increased by relaxing or warming the tissue, by relaxing the arterioles, or by stimulating increased blood flow.

Increased blood volume differentials can be obtained by use of a mechanical pressure device such as a finger cuff or ear lobe clamp. The cuff or clamp is compressed to decrease blood in circulation and blood volume measurements are made with the maximum pressure (minimum blood volume). The cuff or clamp then is released and blood allowed to return to the tissue field while spectral and blood volume measurements are made with the minimum pressure (maximum blood volume). In a variation of this technique a small electric current is used near the tissue field to cause autonomic change in the blood flow to increase blood flow differentials. In yet another variation heat is removed or added at or near the tissue field causing, respectively, autonomic reduction and increase of blood flow. When using the latter techniques to create large blood differentials, e.g. substantially reduced blood flow for a significant time, then substantially increased blood flow for a significant time, spectral signal acquisition can be made over many systole/diastole cycles allowing more time for slow, switched-light sources or sensitive but slow detectors and long-settling-time sense circuits or algorithms to be employed successfully. Different blood volume control methods can be combined if the differential signals developed by use of the systole/diastole flow are inadequate to complete the measurement.

A cuff surrounding the tissue can be inflated using an air pump. Bleed-off, releasing pressure, may be through inherent leakage from the cuff, through a valve, or both. At the appropriate time, the pump is cut off and the fixed bleed-off rate of the inflated structure releases the pressure on the tissue. Referring again to FIG. 2, this device incorporates transparent, inflatable cuff 21, filled by pump 23 through fill tube 22. Cuff 21, when filled, can create a depleted blood condition by clamping finger 6, as described above. Cuff 21 is preferably transparent in wavelengths of interest or contains transparent windows for the light path.

A stiff, compliant collar can be provided at the entrance to the finger-insertion portion of the device, e.g., at the base of the finger. The collar, when pressurized, forces the blood out of the finger for a selected time, which can be selected for the measurement of the minimum blood flow signal acquisition for the particular analyte.

Figure 4A:
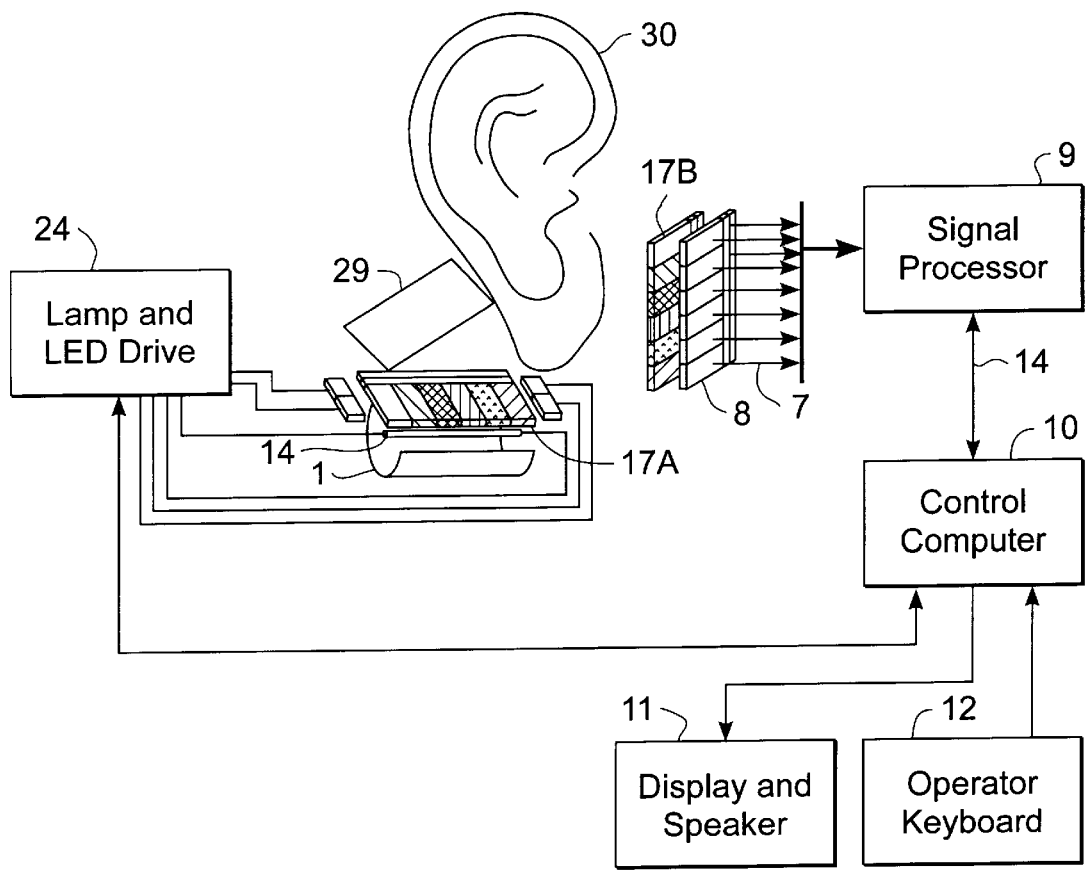
FIGS. 4a and 4b illustrates a fourth embodiment of the invention structured for the non-invasive monitoring of the ear lobe including a tungsten halogen lamp, filters and detectors, and a computer releasable mechanical clamp.

Mechanical pressure can be applied through a clamp mechanism, one example of which is shown in FIG. 4. The clamp preferably limits the maximum pressure which can be applied. The clamp can be released via an electrically actuated release or a fixed mechanical timer, or other methods known in the art. The clamp pressure can be controlled by hand, through an electronic solenoid or through air or fluid pressure. For example, one clamp mechanism compresses an air cylinder to achieve a maximum clamp pressure and after a fixed time bleeds off, releasing the clamp. The rate and amount of compression and decompression can be controlled as precisely as desired by designing an appropriate clamp and test protocol.

The control computer may begin a sequence of measurements using the techniques shown above (electric current, temperature changes, mechanical pressure) for enhancing the differential blood flow or it may instruct the operator to initiate or terminate any or all the differential enhancement techniques detailed above. Clamp, collar or cuff pressure can be completely manually controlled, computer controlled, or manually controlled with computer prompting.

FIG. 4 illustrates a device for monitoring an ear lobe using a tungsten halogen lamp, filters and detectors, and a releasable mechanical clamp. Referring to FIG. 4, this device couples the light source of FIG. 2 with front surface mirror 29 to direct radiant energy through ear lobe 30. Filters 17 and detector 8 are positioned to measure radiant energy passing through ear lobe 30.

Figure 4B:
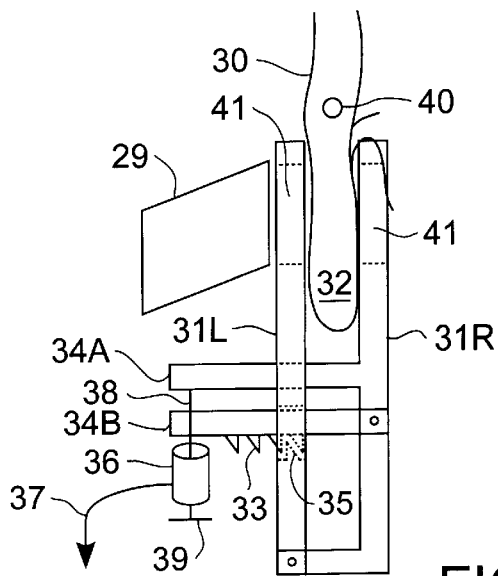

FIG. 4B illustrates clamp 31 which can force blood from ear lobe 30. Pressure in the clamp may be controlled by hand or under computer control, as described above. In one embodiment, the pressure in area 32 of ear lobe 30 is set by moving left member 31L towards right member 31R and latched by a set of teeth 33 on hinged bar 34B engaging straight plate 35 in left member 31L. Under the force of a spring or gravity, teeth 33 remain engaged until released by the action of solenoid 36, energized by control line 37 to move shaft 38, pulling hinged bar 34B upward towards fixed bar 34A and releasing teeth 33, releasing pressure between left member 31L and right member 31R. Shaft 38 can be moved manually by pushing end 39 so an operator can release pressure at any time. This device includes temperature sensor 40 in contact with ear 30 and providing signals to signal processor 9 (not shown). Left member 31L includes a window 41 through which incident light can pass and right member 31R with a corresponding window 41 through which light in the tissue can be detected. The body of clamp 31 is preferably opaque to the wavelengths of interest.

The light transmission through a tissue field and detection can be improved by adding a light blocking device to prevent stray illuminating light reaching the detectors. Referring to FIG. 5, the device of FIG. 1 has been enhanced with finger guide 50 with opaque tabs 51 extending outwardly, generally in a plane between light source 2 and detectors 8. Finger guide 50 may be transparent to wavelengths of interest or may be opaque and incorporate spaces or windows which are transparent to those wavelengths. This allows light passing through the finger to reach detectors 8 but prevents any stray incident light from being detected. FIG. 5 also illustrates use of a positive lens 55 to collect and focus light from the light source onto the tissue field, and a second, complementary positive lens 56 to distribute light to the detection system. Filters 4B have been rearranged to show one alternative filter arrangement to modify the basic light path length in the device. Referring to FIG. 6, the path of light from each filter 4A to each corresponding filter 4B can be modified equally by displacing the entire detector assembly along the tissue field, here by moving down the finger. Light from laser, laser diode, or LED array 25 passes through transparent source window 52, positioned in finger guide 50, through the finger 6 (not shown) and through transparent detector window 53 and detected in detector array 26. The displacement is preferably greater than about 2 cm for a finger and greater than about 8 mm for an earlobe. In general, the displacement is preferably about two to three time the thickness of the tissue field being tested.

In all embodiments, the same volume of tissue is employed both to measure the blood analytes and determine the blood volume, thus providing basis for quantification of analyte per unit volume. The actual volume of tissue is not critical. However, where the tissue field is uniform and blood flow is homogeneous, different regions of the tissue field may be used to quantify the analyte by changing conditions in a portion of the tissue field.

Although the ear lobe and finger are the most convenient tissue fields suitable for measurement by non-invasive instruments of the types described herein, other tissue fields may be desirable sites for monitoring blood analytes for clinical or other reasons. The basic components of this invention may be rearranged to study such sites, including cheek, toe, finger or toe webs, nipples, inner nose, tongue, lip, upper ear portions, region between the hamstring and ankle, and other tissue fields rich in blood.

The method and device of this invention have been described for transmission measurements but the components of the invention may be arranged so that either blood analytes or blood volume or both are measured in reflectance as well. Body tissues are quite transparent to certain light wavelengths for which it may be advantageous to increase the light path by illuminating a tissue region, placing a mirror or back reflector on the other side of the tissue field, then detecting a signal near the light source, thereby doubling the light path relative to the configuration shown in each of the Figures. This may be particularly helpful for thin tissue fields such as the ear lobe. In addition, certain tissues reflect certain wavelengths. Reflectance can thus be used to study skin, muscle, bone and cartilage or other anatomical features which reflect selected wavelengths.

Many configurations not shown in the Figures can be devised by one skilled in the art. For example, the light source might be a monochrometer with no additional dispersive elements coupled to a detector with no dispersive elements, relying on the capability of the monochrometer to deliver a selected wavelength or group of wavelengths. The detector, for almost any of the light sources described above, may be a simple holographic grating coupled to an array of diode detectors, allowing simultaneous measurement of multiple wavelengths.

A general description of the system and method of using the present invention and several preferred embodiments of the present invention have been set forth above. The devices and methods described above and illustrated in the figures represent certain arrangements of the invention but the components may be recombined in other appropriate ways. One skilled in the art will recognize and be able to practice additional variations in the methods described and variations on the device described which fall within the teachings of this invention.

What is claimed is:

1. A non-invasive pulsed infrared spectrophotometer for measuring the concentration of at least one predetermined constituent of a patient's blood, comprising:

an infrared source which emits broadband pulses of infrared light including n different wavelengths, said pulses of infrared light containing energy at each of said n wavelengths being differentially absorbed by said at least one predetermined constituent whereby each predetermined constituent readily absorbs pulses of infrared light at one of said n wavelengths and minimally absorbs pulses of infrared light at another of said n wavelengths, and which directs said pulses of infrared light through an arterial blood vessel of the patient;

at least one infrared detector which detects light at said n wavelengths which has passed through said arterial blood vessel of the patient and has been selectively absorbed by said at least one predetermined constituent and which outputs at least one detection signal;

synchronizing means for synchronizing the application of said pulses of infrared light from said infrared source to said arterial blood vessel of the patient with the systolic and diastolic phases of cardiac cycle of the patient, said synchronizing means including a cardiac monitor and means responsive to an output of said cardiac monitor for modulating said pulses of infrared light so that said infrared light passes through said arterial blood vessel of the patient only during diastolic and systolic time intervals respectively occurring during the systolic and diastolic phases of said cardiac cycle of the patient; and means for determining the concentration of said at least one predetermined constituent of the patient's blood from said at least one detection signal.

2. A spectrophotometer as in claim 1, wherein said modulating means comprises means for electrically modulating said pulses of infrared light so that said infrared light passes through said arterial blood vessel of the patient only during said diastolic and systolic time intervals.

3. A method of non-invasively measuring the concentration of at least one predetermined constituent of a patient's blood, comprising the steps of:

emitting pulses of infrared light at n different wavelengths, pulses of infrared light at each of said n wavelengths being differentially absorbed by said at least one predetermined constituent, each predetermined constituent readily absorbing pulses of infrared light at one of said n wavelengths and minimally absorbing pulses of infrared light at another of said n wavelengths, and directing said pulses of infrared light through an arterial blood vessel of the patient;

detecting light at said n wavelengths which has passed through said blood vessel of the patient and has been selectively absorbed by said at least one predetermined constituent and outputting at least one detection signal;

synchronizing the direction of said pulses of infrared light through said arterial blood vessel of the patient with the systolic and diastolic phases of a cardiac cycle of the patient' and determining the concentration of said at least one predetermined constituent of the patient's blood from said at least one detection signal.

4. A method as in claim 3, wherein said synchronizing step includes the step of modulating said pulses of infrared light so that said infrared light passes through said arterial blood vessel of the patient only during diastolic and systolic time intervals respectively occurring during the systolic and diastolic phases of said cardiac cycle of the patient.

5. A method as in claim 4, wherein said synchronizing step includes the steps of directing light through a tissue of the patient, detecting the light which has passed through said tissue of the patient, and processing a detection output of said light detecting step to determine the phase of said cardiac cycle and to control modulation of said pulses of infrared light in said modulating step.

6. A non-invasive infrared spectrophotometer for measuring the concentration of at least one predetermined constituent of a patient's blood, comprising:

an infrared source which emits broadband infrared light including n different wavelengths, said infrared light containing energy at each of said n wavelengths being differentially absorbed by said at least one predetermined constituent whereby each predetermined constituent readily absorbs pulses of infrared light at least one of said n wavelengths and minimally absorbs pulses of infrared light at at least another of said n wavelengths, and which directs said infrared light through an arterial blood vessel of the patient;

at least one infrared detector which detects light at at least one selected ones of said n wavelengths which has passed through said arterial blood vessel of the patient and has been selectively absorbed by said at least one predetermined constituent and which outputs at least one detection signal;

synchronizing means synchronizing the application of said infrared light from said infrared source to said arterial blood vessel of the patient with the systolic and diastolic phases of a cardiac cycle of the patient, said synchronizing means including a cardiac monitor and means responsive to an output of said cardiac monitor for modulating said infrared light so that said infrared light passes through said arterial blood vessel of the patient only during diastolic and systolic phases of said cardiac cycle of the patient; and means for determining the concentration of said at least one predetermined constituent of the patient's blood from said at least one detection signal.

7. A non-invasive infrared spectrophotometer for measuring the concentration of at least one predetermined constituent of a patient's blood, comprising:

an infrared source which emits broadband infrared light including n different selected wavelengths, said infrared light containing energy at each of said n wavelengths being differentially absorbed by said at least one predetermined constituent whereby each predetermined constituent readily absorbs pulses of infrared light at at last one of said n wavelengths and minimally absorbs pulses of infrared light at at least another of said n wavelengths, and which directs said infrared light through an arterial blood vessel of the patient;

at least one infrared detector which detects light at at least selected ones of said n wavelengths which has passed through said arterial blood vessel of the patient and has been selectively absorbed by said at least one predetermined constituent and which outputs at least one detection signal;

synchronizing means for synchronizing the application of said infrared light from said infrared source to said arterial blood vessel of the patient with the systolic and diastolic phases of a cardiac cycle of the patient, said synchronizing means including a cardiac monitor and means responsive to an output of said cardiac monitor for modulating said infrared light so that said infrared light passes through said arterial blood vessel of the patient only during diastolic and systolic phases of said cardiac cycle of the patient; and means for determining the concentration of said at least on predetermined constituent of the patient's blood from said at least on detection signal.

8. A spectrophotometer as in claim 7 wherein said infrared source includes a tube, said tube including a material adapted to transmit infrared light over a selected range determined by said material, said material being one of quartz, conventional glass, silicon, sapphire, germanium.

9. A spectrophotometer as in claim 7 including a spectral filter associated with said infrared source and adapted to transmit at least one selected wavelengths appropriate for measuring the concentration of a predetermined constituent.

10. A spectrophotometer as in claim 7 wherein said infrared detector includes a filter adapted to transmit at least one selected wavelength appropriate for measuring the concentration of a predetermined constituent.

11. A method of non-invasively measuring the concentration of at least one predetermined constituent of a patient's blood, comprising the steps of:

emitting infrared light at n different selected wavelengths, said infrared light at each said n wavelengths being differentially absorbed by said at least one predetermined constituent, each predetermined constituent readily absorbing said infrared light at at least one of said n wavelengths and minimally absorbing said infrared light at at least another of said n wavelengths, and directing said infrared light through an arterial blood vessel of the patient;

detecting light at selected ones of said n wavelengths which has passed through said blood vessel of the patient and has been selectively absorbed by said at least one predetermined constituent and outputting at least one detection signal;

synchronizing the direction of said infrared light through said arterial blood vessel of the patient with the systolic and diastolic phases of a cardiac cycle of the patient; and determining the concentration of said at least one predetermined constituent of the patient's blood from said at least one detection signal.

12. A method as in claim 11 wherein the step of emitting infrared light includes emitting infrared light over a selected range determined by a material, said material being one of quartz, conventional glass, silicon, sapphire, germanium.

13. A method as in claim 11 wherein the step of emitting infrared light includes filtering to transmit at least one selected wavelength appropriate for measuring the concentration of a predetermined constituent.

14. A method as in claim 11 wherein the step of detecting light includes filtering to transmit at least one selected wavelength approximately for measuring the concentration of a predetermined constituent.

* * * * *